United States Patent [19]

Poirier

[11] 4,086,665

[45] May 2, 1978

[54] ARTIFICIAL BLOOD CONDUIT

[75] Inventor: Victor L. Poirier, Chelmsford, Mass.

[73] Assignee: Thermo Electron Corporation, Waltham, Mass.

[21] Appl. No.: 751,232

[22] Filed: Dec. 16, 1976

[51] Int. Cl.² .......................... A61F 1/24; A61M 1/03
[52] U.S. Cl. ............................................ 3/1.4; 3/1.7;
128/1 D; 128/334 R; 138/109; 138/121;
138/127; 138/138
[58] Field of Search ................. 3/1.4, 1.7, 1; 128/1 D,
128/DIG. 3, 334 R, 334 C, 348; 138/121,
124–127, 137, 138, 109

[56] References Cited

U.S. PATENT DOCUMENTS

| | | | |
|---|---|---|---|
| 2,700,988 | 2/1955 | Smisko | 138/109 X |
| 3,105,492 | 10/1963 | Jeckel | 3/1.4 X |
| 3,272,204 | 9/1966 | Artandi et al. | 3/1.4 X |
| 3,357,432 | 12/1967 | Sparks | 128/334 C |
| 3,374,856 | 3/1968 | Wirt | 138/121 X |
| 3,409,913 | 11/1968 | Kantrowitz et al. | 3/1 |
| 3,688,317 | 9/1972 | Kurtz | 3/1.4 |
| 3,938,528 | 2/1976 | Bucalo | 128/334 C |

OTHER PUBLICATIONS

"An Abdominal Left Ventricular Assist Device: Experimental Physiologic Analyses, II" by William J. Robinson et al., Transactions American Society For Artificial Internal Organs, vol. XIX, 1973, pp. 229–234.
"Relief of Congenital Obstruction to Left Ventricular Outflow with a Ventricular–Aortic Prosthesis" by William F. Bernhard et al., The Journal of Thoracic & Cardiovascular Surgery, vol. 69, No. 2, Feb. 1975, pp. 223–229.

Primary Examiner—Ronald L. Frinks
Attorney, Agent, or Firm—James L. Neal; David W. Gomes

[57] ABSTRACT

An artificial blood conduit comprises two concentrically associated tubes. Convolutions in the tube walls provide flexibility and reduce the tendency to kink. The inner tube is porous to promote the growth of a stable biological interface. The outer tube is impervious to prevent contamination of the blood in locations external to the host body. Rigid reinforcing rings located between the two tubes and affixed to the outer tube, provide the conduit with strength to resist collapse from a wide variety of stress forces. A Dacron cloth sewn tightly around the exterior of the conduit allows tissue fixation without puncturing the conduit. End connectors are provided for different types of anastomoses.

5 Claims, 3 Drawing Figures

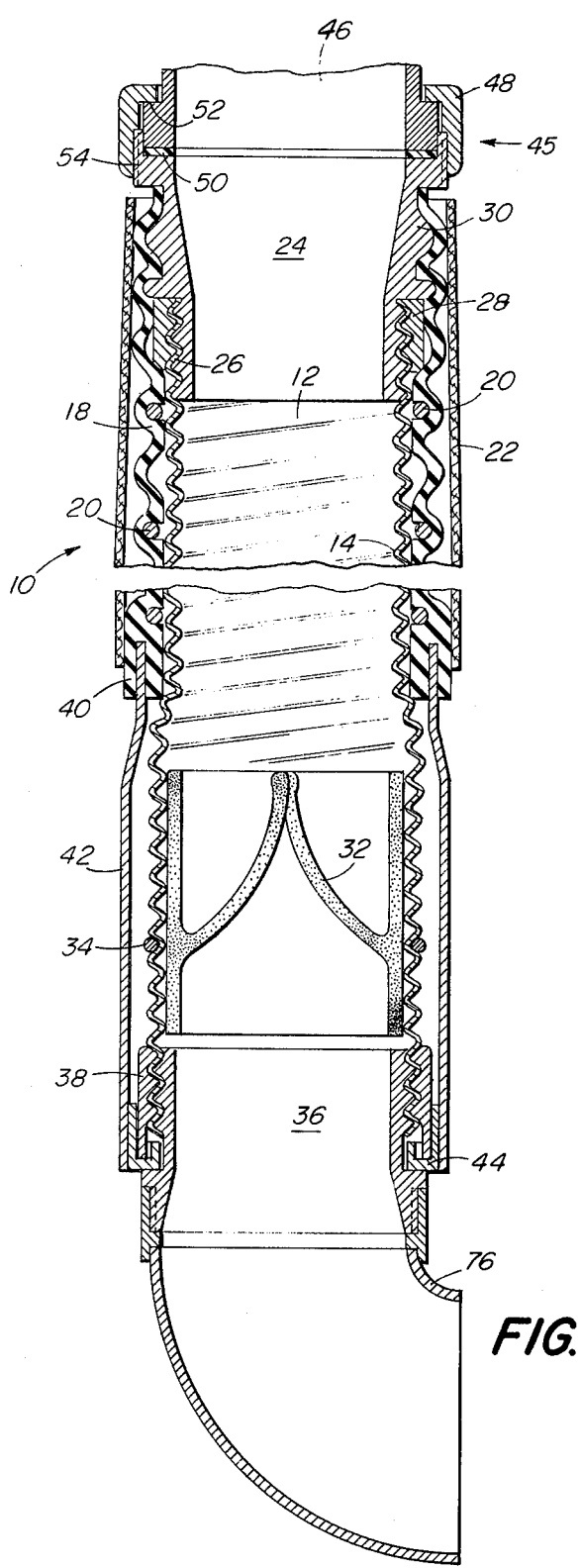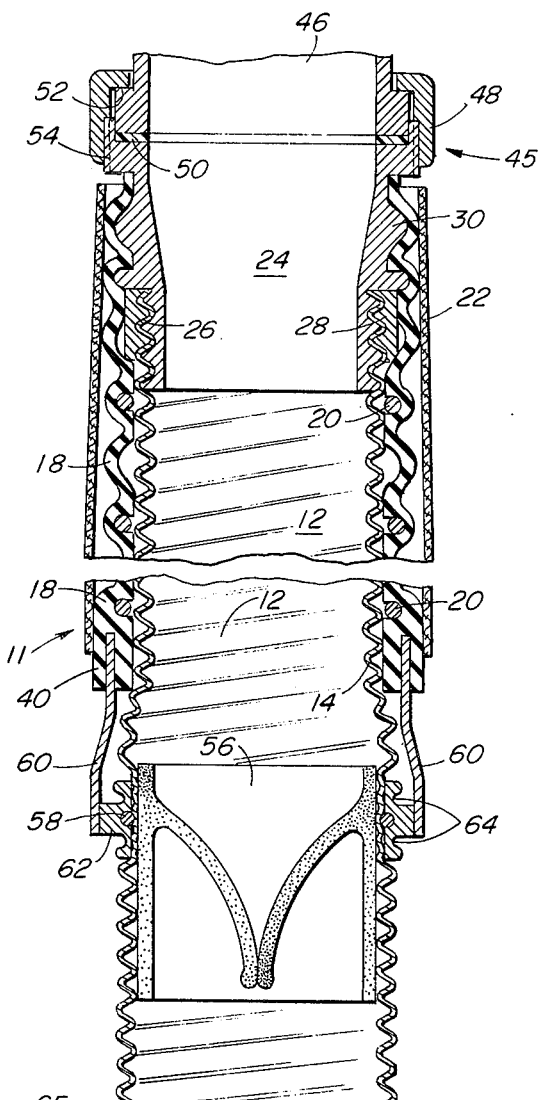
FIG. 1
FIG. 2

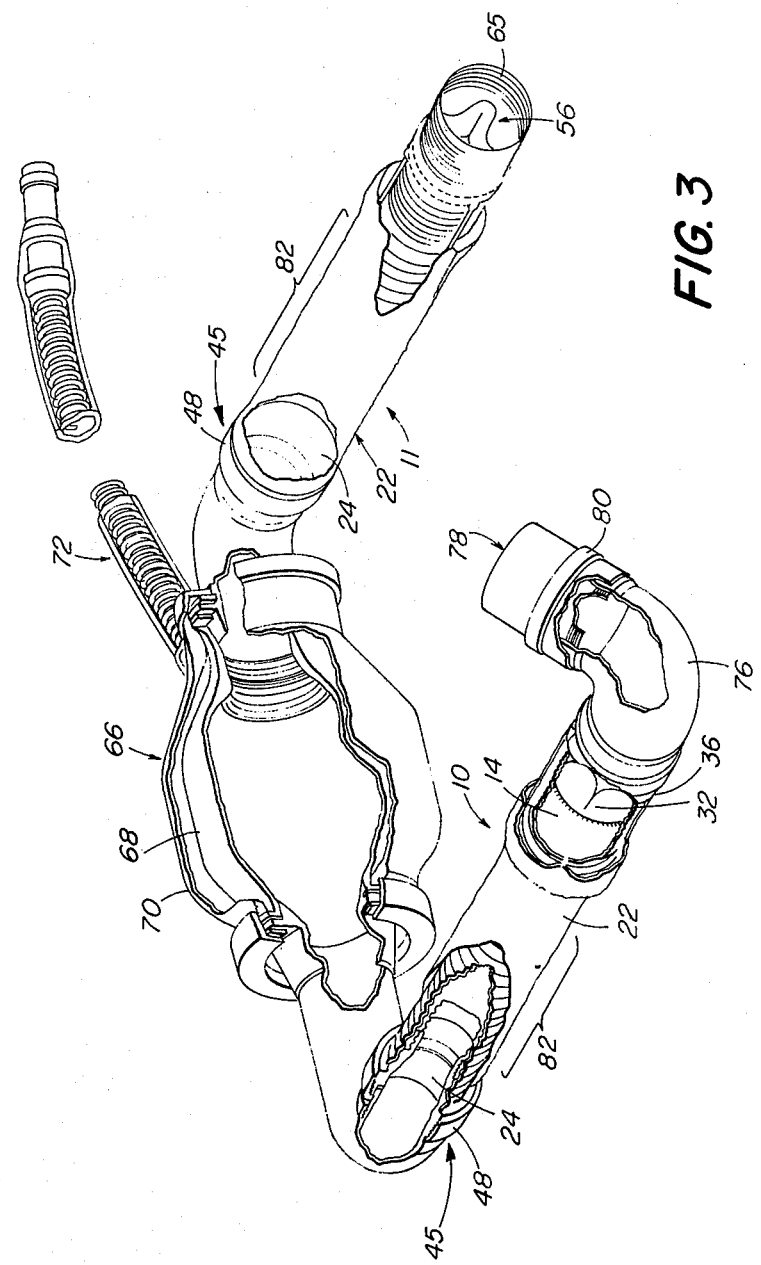

ARTIFICIAL BLOOD CONDUIT

BACKGROUND OF THE INVENTION

The invention described herein was made in the course of or under a contract with the U.S. Department of Health, Education and Welfare.

Artificial blood conduits have become a valuable tool in modern medicine. They are used as permanent and temporary arterial prosthesis. One such use is connecting temporary blood pumps between the left ventricle and a major artery. The demands made on such an artificial blood conduit are great; it must function both inside and outside the host body and be connectable to both the heart and major arteries without introducing contaminants to the body of the host.

Accordingly, it is an object of the present invention to provide an artificial blood conduit which operates externally of the host body and prevents bacteria contamination of the transported blood.

Another object of the present invention is to provide a blood conduit capable of operating internally.

Another object of the present invention is to provide a blood conduit capable of extending from inside the body through the skin to the exterior of the body.

Another object of the present invention is to provide a blood conduit which is flexible and withstands collapse while subject to any variety of physical stresses.

A further object of the present invention is to provide a blood conduit capable of being adapted to a variety of different connectors.

SUMMARY OF THE INVENTION

An artificial blood conduit, capable of both internal and external operation, is provided. The inner surface of the conduit is formed by a porous flexible tube. The wall of the tube is convoluted to facilitate bending without kinking and loss in the lumen diameter. The tube is helically convoluted to mate with an externally threaded rigid end connector and an internally threaded ring. The end connector and ring have threads adapted to mate with each other and to accommodate therebetween the helical convolutions of the tube. An impervious flexible tube surrounds the porous tube. The impervious tube is designed with a convoluted wall to provide flexibility for bending and to inhibit kinking. The impervious tube is a bacteria shield in external application, and its ends may be sealed to the rigid end connectors attached to the porous interior tube. Rigid reinforcing rings are spaced along the conduit between the porous tube and the impervious tube and are affixed to the latter. The rings and their affixation prevent collapse of the conduit under a wide variety of stress forces. A cloth sewn tightly around the outside of the impervious tube forms a base for sutures.

BRIEF DESCRIPTION OF THE DRAWINGS

FIG. 1 is a cross-sectional view of a blood conduit with valve and end connector.

FIG. 2 is a cross-sectional view of the conduit of FIG. 1 with a different termination.

FIG. 3 shows the blood conduits of FIGS. 1 and 2 mounted to a blood pump.

DETAILED DESCRIPTION OF THE DRAWINGS

In reference to FIG. 1, the conduit 10 has an interior surface 12 formed by a flexible polyester fabric tube 14. Fabric tube 14 has a porous and convoluted wall structure to allow the graft to be bent without forming kinks. Coagulated blood, on the porous tube, seals the inner tube 14 and forms a foundation for a stable biological interface between the interior surface 12 and the blood flow. Biologically compatible Dacron tubes with these construction characteristics are commercially available in various diameters from United States Catheter & Instrument Corporation of Billerica, Mass. These tubes are called the DeBakey straight arterial grafts. Types of the grafts typically used are Model Nos. 007068 and 007069. In surgical applications where a patient is taking anticoagulant drugs, it may be desirable to use an arterial graft with a tighter weave fabric of lower porosity. Such a graft, called a Low Porosity Dacron Cooley arterial graft, is available from Meadox Medicals, Inc. of Oakland, N.J.

Surrounding the fabric tube 14 is a flexible impervious tube 18 having convoluted walls to permit flexibility without producing kinks. The tube 18 may be molded from a biologically compatible and non-porous silicone elastomer (e.g., Silastic, medical grade, silicone elastomer No. MDX-4515, made by the Dow Corning Corporation of Midland, Mich.).

Rigid reinforcing rings 20 are positioned between the inner tube 14 and the impervious tube 18. The rings fit into cavities formed in the inner surface of the impervious tube 18 and may be bonded by a biologically compatible adhesive. Individual rings permit the completed assemblage of the fabric tube 14, the impervious tube 18, and the rings 20 to be cut to desired lengths without producing a sharp exposed rigid edge which results when continuous metallic reinforcing is used. The rings 20 afford support for the conduit 10 against radial collapse pressure. Also, the fixed positions of the rings 20 in the impervious tube 18 enables the conduit 10 to resist collapse by forces comprising axial components. The rings 20 may be of a biologically compatible material such as titanium. In one embodiment, a titanium alloy is used comprising titanium with 6% aluminum and 4% vanadium.

A tightly sewn synthetic cloth 22 surrounds the impervious tube 18. The cloth 22 allows skin and musculature fixation in cases where a conduit operates as an external-internal transit means. As the cloth 22 is not bonded directly to the impervious tube 18, skin and musculature may be easily sutured to the cloth 22 without having to puncture the impervious tube 18. In one embodiment, the cloth 22 is biologically compatible Dacron.

Various end connectors are used with the blood conduit 10 to hold tube 14 and 18 in proper relationship and to connect with different natural and artificial members. One such connector 24 is depicted in FIG. 1. The fabric tube 14, having helical convolutions, is threaded onto the end of the connector 24 which defines threads 26 having a pitch matched to the convolutions. A threaded retainer 28 mates with the connector 24 and is tightened thereagainst. The fabric tube is held between the connector 24 and the retainer 28.

The connector 24 also incorporates a means for connection to the impervious tube 18. A portion 30 of the connector 24, adjacent the threads 26, is contoured to mate with the interior surface of the impervious tube 18. The impervious tube 18 can be bonded to this contoured portion 30 to form a bacteria shield at the end of the conduit 10. Thus, in applications where the blood conduit 10 is used to transport blood outside of a patient's body, the combination of the impervious tube 18 and the end connector 24 seals out bacterial contamination to approximate the function of a person's skin.

FIG. 1 also shows a means for terminating the conduit inside a patient's body. In this embodiment, the impervious tube 18 is terminated short of the end of the fabric tube 14. A porcine xenograft valve 32 is located in the fabric tube 14 between the termination 40 of the impervious tube 18 and the end of the fabric tube 14. The valve 32 is affixed by sutures passing through the fabric tube 14 and around a rigid reinforcing ring 34 which maintains the diameter of the valve 32.

A second end connector 36, adapted for connection to another artificial blood conduit, is attached to the end of the fabric tube 14 in the same manner as the end connector 24. More specifically, the fabric tube is threaded onto a portion of the end connector 36 having a thread which mates with the helical convolutions of the fabric tube 14. A retainer 38 is also threaded onto the end connector 36 holding the end of the fabric tube 14 therebetween. Rigid reinforcing members 42 are located between the termination 40 of the impervious tube 18 and the end connector 36. In this embodiment, one end of these members 42 is imbedded in the flexible material of the impervious tube 18 and the other end of the members 42 are affixed to a split ring holder 44. The split ring holder is attached to the end connector 36 by the retainer 38. The portion of the fabric tube 14 between the termination 40 and the end connector 36 is left exposed within the patient's body. This allows for the free diffusion of body fluids into the conduit around the valve 32 to improve the long-term performance of the valve 32. The reinforcing members 42 physically stabilize the exposed portion of the fabric tube 14. Left to its own strength without stabilization, variation in blood pressure caused by either the natural heart or a prosthetic device can cause undesirable oscillations in the exposed portion of the fabric tube 14.

One device for forming a connection with the conduit 10 is shown in FIG. 1 as a quick-connect joint 45. This joint comprises the member 46, the coupling 48 and the Teflon washer 50. The coupling 48 abuts an outward extending annular surface 52 of the member 46 and removably engages the adaptor or connector 24 via the threads 54.

In reference to FIG. 2, the basic structure of the conduit 11 is the same as that of the conduit 10 of FIG. 1. That is, a porous inner tube 14 is enclosed in an impervious tube 18 with reinforcing rings 20 spaced therebetween. Also, one end of conduit 11 is terminated by a connection 24 and quick-release joint 45 in a manner similar to that of the conduit 10. That is, a connector 24 with one end having threads 26 is threaded onto the end of the fabric tube 14. A retainer 28 is applied over the same threads 26 and tightened against the connector 24. The fabric tube 14 is held between the connector 24 and the retainer 28.

The conduit 11 differs from the conduit 10 of FIG. 1 in the type of end termination used at its other end. A porcine xenograft valve 56 is sutured to the fabric tube 14 and the ring or collar 58. The termination 40 of the impervious tube 18 is thickened to mount ends of reinforcing members 60. The other ends of the members 60 are bonded to split ring or collar 62. Both portions of the split ring 62 have a groove around the interior surface for holding the ring 58 and thus the valve 56 in position. The two valves of the split ring 62 are held together after assemblage by sutures in two circumferential grooves 64. The terminal end 65 of the graft 14 is left, unattached, suitable for direct connection by sutures to an artery. This termination of the conduit 11 maintains the full lumen diameter of the conduit and also allows body fluids to have access to the valve 56.

FIG. 3 shows the previously described embodiments of the present invention installed as part of a left ventricular assist device. The conduit 10 of FIG. 1 forms the inlet for an external blood pump 66 and the conduit 11 forms the outlet. The blood pump 66 comprises a flexible polyurethane bladder 68 enclosed by a rigid housing 70. Compressed gas, rhythmically injected and released between the bladder 68 and the housing 70, via the pneumatic drive tube 72, produces pumping action in cooperation with the valves 32 and 56 located in the blood conduits 10 and 11. Operation of the blood pump 66 is described in detail in the U.S. Pat. Application Ser. No. 647,842, filed on Jan. 9, 1976 for "Volumetrically Efficient Blood Pump" in the name of Victor L. Poirier. The joints 45 connect the conduits 10 and 11 to the blood pump 66. The quick-connect feature expedites surgical assembly.

One means of performing the left ventricular assist function is to connect the blood pump 66 between the left ventricle of the heart and a major artery, bypassing the aortic valve. A curved section 76 is affixed to the end connector 36 of inlet conduit 10. The curved section 76 is attached directly to the end connector 36 and a rigid inlet tube 78. Upon implantation, the inlet tube 78 is inserted through a hole in the heart muscle. The rigidity of the inlet tube 78 maintains the lumen of the passageway during the natural contractions of the heart. The inlet tube 78 is held in place by suture ring 80 which is sutured to the heart around the hole in the heart muscle and is also circumferentially bound to the inlet tube 78. The curved section 76 maintains the lumen of the connection while making a sharp bend immediately upon exiting the left ventricle of the heart to adapt to typical anatomy. The outlet of the pump 66, the conduit 11, is connected to a major artery. The connection is usually made to the descending thoracic aorta by suturing one end of conduit 11 directly thereto. The conduits 10 and 11 thus extend through the wall of the chest cavity between the natural heart and the pump 66.

With the aforementioned internal connections and an externally located blood pump 66, the conduits 10 and 11 pass through the chest within regions 82 and function outside the body while inhibiting contamination of the blood or infection at the point of incision. Skin and musculature tissue at the incision are sutured to the cloth 22.

As various changes could be made in the above construction without departing from the scope of the invention, it should be understood that all matter contained in the above description or shown in the accompanying drawings shall be interpreted as illustrative and not in a limiting sense.

I claim:
1. A blood conduit comprising:
 a flexible inner tube for conducting a flow of blood and having a porous wall for permitting the development of a biologically stable interface between the interior surface of said inner tube and blood flow therethrough, said inner tube having a convoluted wall structure for providing flexibility without kinking;
 a flexible, non-porous outer tube concentrically enclosing said inner tube, for preventing contamina- tion, said outer tube having a convoluted wall structure for providing flexibility without kinking;

rigid ring means spaced along said conduit and located concentrically between said outer tube and said inner tube for providing radial strength to said conduit; and means affixing said ring means to said outer tube for providing said conduit with strength to resist collapse forces with axial components.

2. The conduit of claim 1, further comprising:

a rigid tubular end connector being open at both ends, one end being adapted to receive the convoluted wall structure of said inner tube around the outer surface thereof;

a rigid coupling for firmly holding said convoluted wall structure against the outer surface of said end connector; and means on said end connector for receiving and holding the wall structure of said outer tube.

3. The conduit of claim 1, wherein said convoluted wall structure of said inner tube defines a circumferential helix, further comprising, a rigid tubular end connector open at both ends, one end of said connector having a circumferential exterior thread for mating with said circumferential helix, a rigid coupling having a circumferential interior thread of the same pitch as said circumferential exterior thread for mating with said exterior thread and engaging said inner tube between said exterior and interior threads, and a plurality of exterior circumferential ridges opposite said exterior thread on said end connector, said plurality of edges being engageable with said convoluted wall structure of said outer tube for forming a fluid-tight seal therebetween.

4. The conduit of claim 1, further comprising:

a heart valve located inside said inner tube, near one end thereof, and circumferentially affixed to said inner tube for substantially preventing fluid flow in one direction through said inner tube;

said outer tube having a terminal end short of said heart valve;

a plurality of members one end of each being affixed to said terminal end of said outer tube and the other end of each extending past said heart valve;

an annular holder affixed to said other ends of said plurality of members;

a rigid tubular end connector for circumferentially gripping said inner tube adjacent said heart valve, on the side thereof opposite said terminal end of said outer tube; and said annular holder being attachable to said end connector.

5. The conduit of claim 1, further comprising:

a heart valve located in one end of said inner tube and circumferentially affixed thereto for preventing fluid flow in one direction through said inner tube;

a first rigid collar concentrically affixed to said heart valve and said inner tube external to said inner tube;

said outer tube having a terminal end short of said heart valve;

a plurality of members, each having one end affixed to said terminal end of said outer tube; and a second rigid collar circumferentially engaging said first collar, said second collar being affixed to the other ends of said plurality of members for holding said first collar and said heart valve in fixed relation with said terminal end of said outer tube.

* * * * *